(12) United States Patent
Schanen et al.

(10) Patent No.: US 8,278,375 B2
(45) Date of Patent: Oct. 2, 2012

(54) MIXED PHOSPHONATE FLAME-RETARDANTS

(75) Inventors: Vincent Schanen, Lyons (FR); Dwight Shamblee, North Charleston, SC (US); Gleb Priimov, Coventry (GB); Julie Ann Salter, Dudley (GB)

(73) Assignee: Rhodia UK Limited, Watford Hertfordshire (GB)

( * ) Notice: Subject to any disclaimer, the term of this patent is extended or adjusted under 35 U.S.C. 154(b) by 889 days.

(21) Appl. No.: 11/988,376

(22) PCT Filed: Jul. 5, 2006
(Under 37 CFR 1.47)

(86) PCT No.: PCT/FR2006/001598
§ 371 (c)(1),
(2), (4) Date: Feb. 27, 2009

(87) PCT Pub. No.: WO2007/006915
PCT Pub. Date: Jan. 18, 2007

(65) Prior Publication Data
US 2012/0123025 A1    May 17, 2012

Related U.S. Application Data

(60) Provisional application No. 60/695,882, filed on Jul. 5, 2005.

(51) Int. Cl.
*C08K 5/5317* (2006.01)
*C08K 5/5333* (2006.01)
*C08K 5/5357* (2006.01)
*C08L 63/00* (2006.01)
*C07F 9/40* (2006.01)

(52) U.S. Cl. ........ 524/123; 524/115; 524/116; 524/117; 524/121; 524/130; 524/131; 524/147; 524/706; 524/710; 523/451; 558/70; 558/73; 558/77; 558/82; 558/83; 558/119; 558/120; 558/134; 558/146; 558/147; 558/155; 558/156; 558/161; 558/214; 568/8; 568/12; 428/403

(58) Field of Classification Search .................. 252/601, 252/608, 609; 428/403, 404, 406; 523/451, 523/456; 524/115, 116, 117, 121, 123, 130, 524/131, 136, 139, 147, 706, 710; 558/70, 558/73, 77, 82, 83, 87, 89, 117, 118, 119, 558/120, 134, 146, 147, 155, 156, 161, 163, 558/164, 165, 177, 194, 197, 207, 214, 217; 568/8, 12

See application file for complete search history.

(56) References Cited

U.S. PATENT DOCUMENTS

| 2,880,224 A * | 3/1959 | Smith, Jr. ...................... 558/136 |
| 3,600,339 A * | 8/1971 | Baranauckas et al. ........ 521/168 |
| 7,067,076 B2 * | 6/2006 | Wo et al. ...................... 252/609 |
| 2005/0038144 A1* | 2/2005 | Wo et al. ...................... 524/115 |

FOREIGN PATENT DOCUMENTS

| EP | 15703 A * | 9/1980 |
| EP | 0 758 654 B1 | 2/1997 |
| WO | WO 2005/012420 A2 | 2/2005 |

* cited by examiner

*Primary Examiner* — Michael J Feely
(74) *Attorney, Agent, or Firm* — SNR Denton US LLP

(57) ABSTRACT

Mixtures of three types of linear, branched or cyclic phosphates are useful flame retardants, especially for thermoplastic resins or as functional additives in polymer matrices.

19 Claims, No Drawings

MIXED PHOSPHONATE FLAME-RETARDANTS

CROSS-REFERENCE TO EARLIER APPLICATIONS

This application is a national phase of PCT/FR 2006/001598, filed Jul. 5, 2006 and designating the United States (published in the French language on Jan. 18, 2007, as WO 2007/006915 A1; the title and abstract were published in English), which claims benefit under 35 U.S.C. 119(e) of U.S. Provisional Application No. 60/695,882, filed Jul. 5, 2005, each hereby expressly incorporated by reference in its entirety and each assigned to the assignee hereof.

The present invention proposes a novel product comprising a mixture of three types of linear, branched or cyclic phosphonates, a process for synthesizing this novel product, and the use of such a product as a flame retardant, especially for thermoplastic resins, or functional additives in polymer matrices.

DESCRIPTION OF THE PRIOR ART

Flame retardants are incorporated into many products for safety purposes in order to control fire propagation. Flame retardants may act, for example, by causing the rapid extinction of flames, or by making the product difficult to ignite. Although flame retardants have conventionally been used for treating textiles, furniture fabrics, etc. and have been incorporated into foams, paints and resins such as epoxy resins, many other applications are currently being actively investigated, in particular in the electronics, automotive, aerospace and construction industries.

It is known practice to use phosphonates as flame retardants. For example, U.S. Pat. No. 3,789,091, EP 0 758 654 and WO 2005/02412 describe a process for synthesizing cyclic phosphonate products. On account of the increasing use and demand for flame retardants, there is a need to propose a more economical process for the industrial synthesis of these phosphonate-based agents. Furthermore, in order to satisfy the various needs of the many diverse applications in which these agents are conventionally used and/or are beginning to be used, there is a need to provide a wider range of phosphonate compounds than has been available to date. For example, flame retardants in various physical forms and of various viscosities may be necessary, depending on the application. Although they are useful for conferring flame-retardant properties in thermoplastics, phosphonate-based flame-retardant additives have drawbacks that limit their use. Furthermore, flame-retardant products with improved thermal and hydrolytic stabilities are very desirable for various applications.

It has been observed that a large number of conventional flame-retardant additives have a tendency to migrate and/or to volatilize from thermoplastic matrices, over time. Migration of the flame-retardant additive leads to the article finally losing its flame-retardant properties. Certain flame retardants may produce or contain volatile compounds, which, on contact with glass, in particular cold glass, cause fogging. This is particularly undesirable when the flame retardant must be used in automotive or aerospace applications.

Another drawback of the known phosphonate-based flame-retardant additives is their hygroscopic properties, which lead thermoplastic articles incorporating these additives to absorb moisture or water over time. Furthermore, the known phosphonate-based flame-retardant additives have low thermal stability. It is known that the additives decompose at various temperatures of processing of the thermoplastics, and in particular during the process of extruding thermoplastics.

Furthermore, the use of phosphates containing halogens as flame retardants is considered environmentally undesirable.

There is thus a need to develop flame retardants that can overcome all the drawbacks under consideration.

The present invention proposes a phosphonate-based flame-retardant additive that avoids the drawbacks of the known phosphonate-based flame-retardant additives, to produce useful compositions. The invention also relates to a process for preparing a phosphonate-based flame-retardant additive.

Consequently, the present invention proposes a novel halogen-free product comprising a mixture of three types of phosphonate components (A), (B) and (C) as defined:

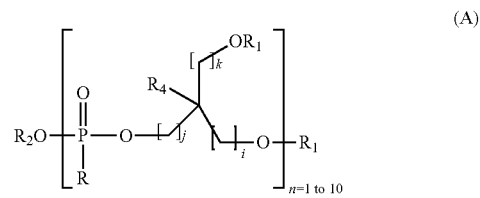

in which:

j and k are, independently, equal to 1 to 10,

R is a linear, branched or cyclic alkyl or alkenyl group, $R_4$ is a proton or a linear, branched or cyclic alkyl or alkenyl group, $R_2$ is a linear, branched or cyclic alkyl or alkenyl group or the cyclic phosphonate (I):

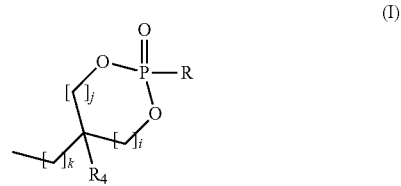

in which i, j, k, R and $R_4$ are as described above, $R_1$ is

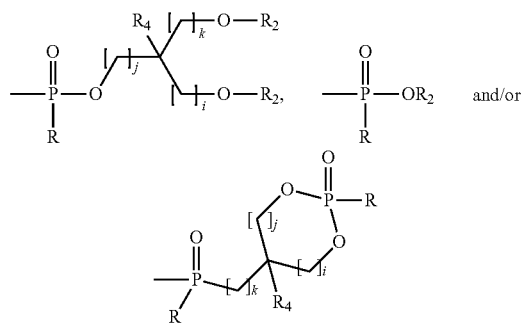

in which $R_2$, $R_4$, R, j and k are as described above;

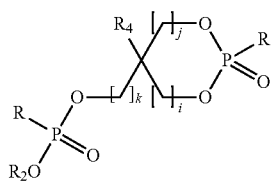

(B)

in which $R_2$, $R_4$, R, i, j and k are as described above;

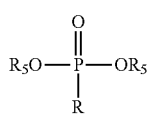

(C)

in which:

R is a linear, branched or cyclic alkyl or alkenyl group as described above, $R_5$ is a linear, branched or cyclic alkyl or alkenyl group.

The product is preferably defined as being a mixture of (A), (B) and (C) in the following mole ratios:

| Component | Minimum % | Maximum % | Typical % |
|---|---|---|---|
| (A) | 1 | 99 | 50 |
| (B) | 1 | 99 | 40 |
| (C) | 0 | 25 | 10 |

Preferably, the mole ratios between (A), (B) and (C) are:

| Component | % |
|---|---|
| (A) | 30-55 |
| (B) | 30-40 |
| (C) | 5-15 |

One of the preferred ratios (A)/(B)/(C) is:
(A)=50%
(B)=40%, and
(C)=10%.
One of the preferred products is:
i, j, k=1
$R_4$=ethyl
R=hexyl
$R_5$=butyl
$R_2$=butyl or (I)
Another preferred product is:
i, j, k=1
$R_4$=ethyl
R=butyl
$R_5$=butyl
$R_2$=butyl or (I)
The invention also proposes a process for synthesizing the defined mixture of (A), (B) and (C), comprising the following steps:
a) reacting a triol of general formula (IV) with a dialkyl phosphite of general formula (V) to give the intermediate (VI):

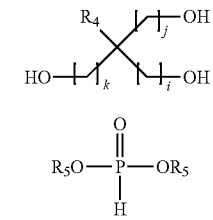

(IV)

(V)

b) reacting the intermediate (VI) with a linear, branched or cyclic alkene or alkyne or a substituted alkene or alkyne bearing at least one unsaturated bond, in the presence of a non-oxidizing radical initiator, to partially convert the phosphite into phosphonate, c) removal of bicyclic phosphite produced in the preceding step, via distillation, especially in the presence of a solvent, d) reaction of the intermediate with a linear, branched or cyclic alkene or alkyne or a substituted alkene or alkyne bearing at least one unsaturated bond, in the presence of a radical initiator, to obtain total conversion of the intermediate, e) optional purification of the product obtained in step d), for example by distillation.

The intermediate (VI) corresponds to a mixture of components (A'), (B') and (C').

The first chemical reaction of step a) is a transesterification between a dialkyl phosphite and a triol, preferably catalysed with a base, for example a metal alkoxide such as a sodium or potassium alkoxide; or any non-nucleophilic organic base, such as 1,8-diazabicyclo[5.4.0]undec-7-ene: DBU.

The mole ratio of the triol to the dialkyl phosphite is typically in the range from 1:1.5 to 1:10, preferably from 1:1.6 to 1:2.5 and most preferably from 1:1.7 to 1:1.9.

The mole ratio of the base to the dialkyl phosphite is typically in the range from 0.01:1 to 0.5:1, preferably from 0.02:1 to 0.1:1 and most preferably from 0.03:1 to 0.05:1.

In the most preferred embodiment, the first reaction is performed with TMOP as triol and DBHP as dialkyl phosphite:

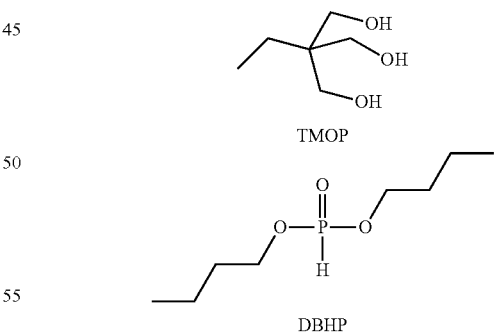

TMOP

DBHP

To obtain a good conversion, the reaction mixture should preferably be heated, and the alcohol generated during the transesterification should be removed during the reaction. This operation may be performed using any conventional distillation process; performing the reaction under reduced pressure is a suitable process for removing the alcohol. This step is performed at a temperature in the range from 5 to 200° C., preferably between 20 and 150° C. and most preferably between 40 and 130° C.

This step is performed under a reduced pressure of between 1 and 900 mbar, preferably between 5 and 500 mbar and most preferably between 10 and 30 mbar.

During the reaction, all the dialkyl phosphite may be introduced in a single portion or continuously over several hours. If the addition is continuous, the volume efficiency is significantly improved. The base is added portionwise during the process. The use of a solvent is possible.

In the most preferred embodiment, the first reaction is performed at a pressure of from 10 to 20 mbar, while the temperature is slowly increased from 40-50° C. to 110-125° C. A solution of sodium methoxide in methanol is preferably used as base. The butanol formed is distilled off continuously.

The preceding description indicates that during the reaction of the dialkyl phosphite with a polyol, the reaction mixture changes towards the component of type (B') when the reaction is performed so as to be complete. We have now found that, even after a long reaction time in attempts to obtain the thermodynamic product of type (B'), the components of type (A') and (C') are still present in significant amounts, occasionally exceeding 25% of the weight of the product.

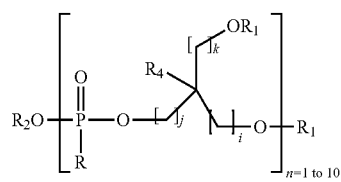

(A')

(I) being

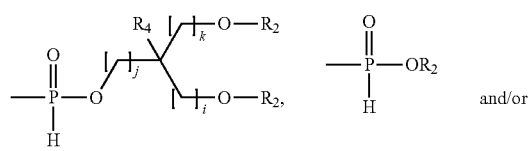

(I)

$R_1$ being:

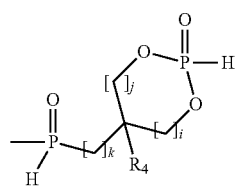

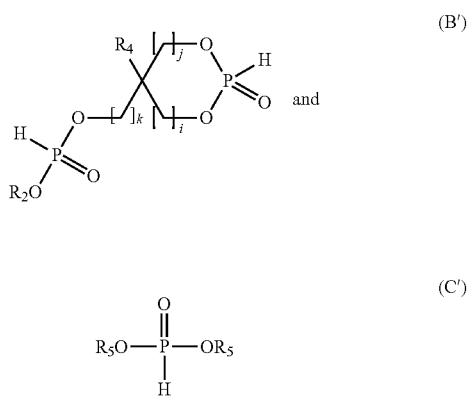

(B')

and

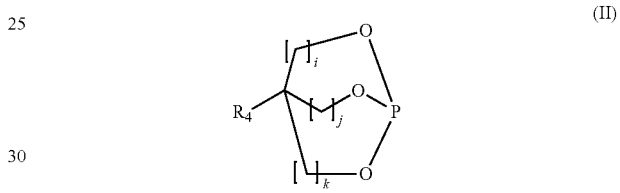

(C')

During this step, a side reaction forms bicyclic phosphites of general formula (II)

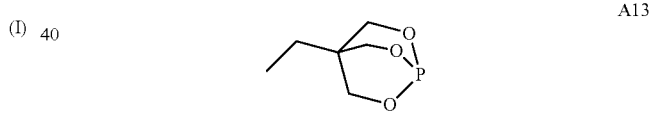

(II)

Certain bicyclic phosphites (II) are known as being toxic.

When the triol used to perform the reaction is TMOP, the impurity (II) generated is also known as A13.

A13

It is not possible to remove the bicyclic phosphite at this stage via distillation on account of the low thermal stability of the intermediates (A'), (B') and (C') and on account of the high boiling point of the bicyclic phosphite (b.p. A13=110° C. at 8 mmHg). Furthermore, the more the reaction mixture is heated, the greater the amount of bicyclic impurity generated.

The other conventional manner for removing the bicyclic phosphite is by reacting it with a halohydrocarbon, for example bromobutane (Arbusov reaction). This technique is suitable but not ideal, given that it leads to a halogenated product. The halogenated product is environmentally undesirable, in particular since the new regulations prohibiting certain halogenated flame retardants.

The second step b) of the reaction consists of a free-radical alkylation of the P—H bonds of the intermediates (A'), (B') and (C') with alkenes or alkynes.

Free-radical addition reactions of this type are known, these reactions being brought about by radical initiators such as peroxides, for example di-tert-butyl peroxide, or azo initiators.

However, the use of peroxide initiators leads to the formation of high levels of bicyclic phosphate (III):

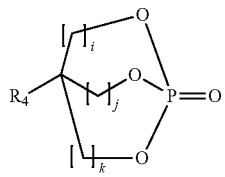
(III)

Certain bicyclic phosphates (III) are known as being toxic. If the triol used to perform the reaction is TMOP, the toxic impurity (III) generated is also known as A13 oxide.

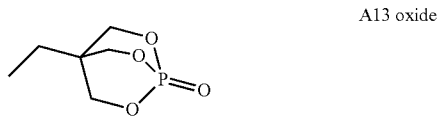
A13 oxide

On account of its high boiling point, the bicyclic phosphate cannot be removed by distillation. The conventional manner for removing this side product is by washing with water or aqueous bases such as sodium hydroxide or sodium carbonate. The washing step has two main drawbacks; it generates a large amount of waste, and the final product inevitably contains residual water, which may adversely affect its thermal stability.

In order to avoid the formation of bicyclic phosphates, it is possible to use a non-oxidizing initiator, for instance AIBN or VAZO 67, 2,2'-azobis(2-methyl-butyronitrile). However, initiators of these types are not as efficient as peroxides, and, even using a large amount of initiator, it is not possible to obtain complete conversion of the P—H bond into a P—C bond.

We have now discovered that the problems of the impurities of bicyclic phosphite/phosphate can be solved by using a first non-oxidizing initiator to obtain a certain degree of conversion (at least 10% of P—H converted into P—C), which gives the product sufficient thermal stability to allow the removal of the bicyclic phosphite by distillation. Next, the reaction is continued and total conversion may be obtained with a more efficient initiator such as di-tert-butyl peroxide. Unexpectedly, no additional bicyclic phosphite is generated during this final step. The product prepared in this manner has a very low content of bicyclic phosphite (II) and of bicyclic phosphate (III), typically less than 0.1% m/m, which makes the washing step superfluous.

For the second chemical reaction of step b), the mole ratio of the dialkyl phosphite (used in step a)) to the alkene or alkyne is typically in the range from 1:10 to 1:100, preferably from 1:5 to 1:10 and most preferably from 1:1 to 1:1.5.

The mole ratio of the dialkyl phosphite (used in step a)) to the non-oxidizing initiator is typically in the range from 1:1 to 1:0.5, preferably from 1:0.5 to 1:0.1 and most preferably from 1:0.1 to 1:0.03.

This step is generally performed at a temperature in the range from 40 to 200° C., preferably between 60 and 150° C. and most preferably between 80 and 130° C.

This step is generally performed at a pressure in the range from 1 to 50 bar, preferably between 1 and 10 bar and most preferably between 1 and 5 bar.

The alkene or alkyne and the non-oxidizing initiator may be added continuously during the reaction.

The non-oxidizing initiator may be dissolved in a solvent or in the alkene reagent when it is liquid. The use of a solvent is possible, for instance toluene or cyclohexane.

The bicyclic phosphite is generally removed by distillation/revaporization in step c). This step may be performed in the presence of a solvent, preferably a non-nucleophilic solvent, such as toluene, cyclohexane or dichloromethane.

This step is generally performed at a temperature in the range from 80 to 200° C., preferably between 100 and 150° C. and most preferably between 120 and 145° C.

This step is generally performed under reduced pressure in the range from 1 to 900 mbar, preferably between 5 and 500 mbar and most preferably between 0.5 and 5 mbar.

For the third chemical reaction of step d), the mole ratio of the dialkyl phosphite (used in step a)) to the alkene or alkyne is typically in the range from 1:10 to 1:100, preferably from 1:5 to 1:10 and most preferably from 1:0.1 to 1:0.5.

The mole ratio of the dialkyl phosphite (used in step a)) to the peroxide initiator is typically in the range from 1:1 to 1:0.5, preferably from 1:0.5 to 1:0.1 and most preferably from 1:0.1 to 1:0.03.

This step is generally performed at a temperature in the range from 40 to 200° C., preferably between 60 and 150° C. and most preferably between 110 and 130° C.

This step is generally performed at a pressure in the range from 1 to 50 bar, preferably between 1 and 10 bar and most preferably between 1 and 5 bar.

The alkene or alkyne and the peroxide initiator may be added continuously during the reaction.

The peroxide initiator may be dissolved in a solvent or in an alkene/alkyne when it is liquid.

The use of a solvent is possible, for instance toluene or cyclohexane.

In the most preferred embodiment, the second reaction of step b) is performed at a pressure of 1.5 bar, with a temperature increasing slowly from 110° C. to 125° C. VAZO 67 is used as non-oxidizing initiator. 1-Hexene is used as alkene.

The revaporization step is performed at 1 mbar and from 140 to 145° C.

In the most preferred embodiment, the third reaction of step d) is performed at a pressure of 1.5 bar, with a temperature increasing slowly from 125° C. to 135° C. Di-tert-butyl peroxide is used as initiator. 1-Hexene is used as alkene. A final revaporization is performed at 150-170° C. at 5 mbar.

The invention also relates to the use of a phosphonate product as described previously as, or in relation with, a flame retardant. Specifically, the product of the invention affords flame-retardant properties to plastics, in particular thermoplastics. Representative but non-limiting examples include acrylonitrile-butadiene-styrene, polystyrene, polyamide, polyethylene, polypropylene, polycarbonate, PVC, polyethylene terephthalate, polybutylene terephthalate, and the like.

The phosphonate product may also be used as flame retardant in, or in relation with, epoxy resins, polyurethane resins and composites, phenolic resins, paints, varnishes and textiles.

Furthermore, for the use as flame retardant, the phosphonate product according to the present invention may be absorbed onto an oxide, hydroxide or mineral salt of high porosity. The inorganic compounds that may be used include oxides or hydroxides of silicon, of aluminium, of magnesium, of tin, of iron, of zirconium and of titanium, and silicates such as talc and mica. The product obtained in this manner may be used as flame-retardant additive for thermoplastics. Representative but non-limiting examples of thermoplastics that may be made flame-retardant in this manner include acrylonitrile-butadiene-styrene, polystyrene, polyamide, polyethylene, polypropylene, polycarbonate, PVC, polyethylene terephthalate, poly-butylene terephthalate and the like.

The flame-retardant materials of the present invention may be used in any conventional applications, for example in the automotive, aerospace and construction industries.

The phosphonate product according to the present invention may be used for coating particular inorganic materials, for improving the dispersibility of such materials in thermoplastic resins. Such a coating may greatly increase the compatibility and thus the dispersibility of such particular inorganic materials in such resins, which is often insufficient on account of the hydrophilic nature of the inorganic pigments or fillers and of the hydrophobic nature of thermoplastic resins. The coating materials obtained in this manner may be used as functional additives for improving the properties of a polymer matrix, for example as UV-light absorbers, dyes, opacifiers and the like in various thermoplastics.

Representative but non-limiting examples of particular inorganic materials that may be treated include materials that are used as pigments, fillers and extenders. Examples include titanium dioxide, zinc oxide, antimony-based pigments, barium-based pigments, calcium-based pigments, zirconium-based pigments, chromium-based pigments, iron-based pigments, lead-based pigments, zinc sulfide, lithopone, silica, silicates such as talc and mica, aluminium oxides and hydroxides, magnesium oxides and hydroxides, sulfates such as gypsum and barium sulfate, carbonates such as calcium carbonate, borates such as zinc borate, or clays.

EXPERIMENTAL SECTION

Example 1

Preparation of a mixture A'/B'/C'
(Trans-Esterification Reaction)

The equipment used is a 1-litre jacketed tank, with an associated circulating unit and heater. The tank is equipped with a thermocouple and a side arm leading to a condenser and a collector for collecting the butanol distillate. The reagents are stirred using a four-blade PTFE agitator. The system is airtight with a three-way nitrogen line to refill the tank after it has been placed under reduced pressure.
Composition:

| Reagent | Weight | Moles | Mole ratio |
|---|---|---|---|
| TMOP | 670 | 5 | 1 |
| DBHP (1) | 850 | 4.38 | 0.875 |
| NaOMe 25% (1) | 30 | 0.139 | 0.028 |
| DBHP (2) | 847.6 | 4.37 | 0.875 |
|  |  |  | (total DBHP: 1.75) |
| NaOMe 25% (2) | 36 | 0.167 | 0.033 |
|  |  |  | (total NaOMe: 0.06) |

Process:

TMOP and DBHP (1) are introduced. The mixture is heated to 60° C. to dissolve the TMOP. The NaOMe 25% (1) is then added and the mixture is cooled to 30° C. A full vacuum is then applied and the tank temperature is slowly increased. The butanol begins to distil off at approximately 40° C. All the butanol is removed in approximately 10 hours.

The DBHP (2) is added continuously over 6 hours. The NaOMe 25% is also divided into 3 equal portions and is added after about 20% of the butanol has been removed, after about 40% of the butanol has been removed, and after about 60% of the butanol has been removed.

The temperature remains at about 60° C. until the addition of DBHP is stopped, and a higher temperature is then required to distil off the residual butanol (continuous distillation at a rate of about 100 g/h for a further ¾ hours, while gradually increasing the temperature when the distillation slows down).

The maximum tank temperature is not greater than 125° C.

Mean product: 1.3 kg of product are obtained.

The product is then analysed by $^{31}P$ NMR (insertion of $D_2O$).

Several tests were performed under these conditions.

| Test number | TMOP (ratio) | DBHP (ratio) | NaOMe (25%) (ratio) | A13 | B' | C' | A' |
|---|---|---|---|---|---|---|---|
| 639js371 | 1 | 1.75 | 0.055 | 0.2 | 40.7 | 8.3 | 50.8 |
| 639js372 | 1 | 1.75 | 0.055 | 0.2 | 39.1 | 9.3 | 51.3 |
| 672js380 | 1 | 1.75 | 0.055 | 0.2 | 37.6 | 9.2 | 53.1 |
| 672js382 | 1 | 1.75 | 0.055 | 0.2 | 40.5 | 10.5 | 48.8 |

Example 2

Preparation of a Mixture A/B/C and
A'/W/C'(Alkylation Reaction)

125 kg of intermediate A'B'C' prepared according to Example 1 are introduced under vacuum into a 50-gallon reactor. The reactor is then inertized by applying a vacuum and repressurizing with nitrogen, 3 times. The mixture is heated to 105-110° C.

With an $N_2$ purge of 200 l/h, the pressure increases to 1.5 bar. A solution containing 50% by weight of Vazo-67 in toluene is prepared in the laboratory and divided into 244-g portions. Each portion is added over 30 minutes, with a simultaneous introduction of hexene over 9 hours 50 minutes. After the initial exothermicity, which raises the tank temperature to 115° C., the temperature is maintained in the range from 106 to 113° C. This gives a conversion of P of 67.1% into product.

This is followed by adding 13.5 portions of 418 g of Vazo-67 solution at 50% by weight in toluene, over 7 hours, without additional introduction of hexene. Each portion is added over 30 minutes. The temperature is maintained at about 110° C. for the first 3.5 hours and then gradually raised to 127-130° C. In the totality of the 13.5 portions of 418 g is added an additional portion of 200 g of initiator, added between portions 12 and 13. The reactor is allowed to cool. At this stage, the conversion of product is 85% to 88% from P—H into P—C.

The first part of the alkylation takes 21.25 hours to be performed completely.

Distillation

The mixture obtained from the alkylation reaction is distilled in order to remove the A13, to obtain an amount of less than 0.1% by weight.

Conditions: the mixture is heated to 160-180° C. with a pressure of 1 to 3 mbar. The distillation is stopped when about 10% of the mass has been distilled off.

| Components | Starting material | After boiling | Distillate |
|---|---|---|---|
| A13 | 0.455 | 0.05 | 16.1 |
| A + B + C | 84.4 | 86.2 | 83.9 |
| A' + B' + C' | 15.1 | 14 | |
| Weight of starting material | 205 | | |
| Weight of correct product after boiling | 177.3 | | |
| Weight of distillate | 22.6 | | |
| Weight loss/condenser (estimated) | 5 | | |

Second Alkylation Reaction:

A 50-gallon reactor is charged with 150 to 160 kg of product ABAA'B'C' prepared according to the preceding step.

Aliquots of $^tBuO_2$ (267 g) are added at one-hourly intervals over 20 to 30 minutes for the first 4 hours of this part of the alkylation. The hexene charge is introduced at between 1.3 and 2.4 kg/h (total: 12.8 kg). The reaction temperature is in the range from 129 to 133° C. over 9 hours. The conversion of A'B'C' is greater than 98% into ABC.

Final Distillation

A vacuum of about 50 mbar is applied to the reactor, and an initial distillation is observed, but when the reaction mixture is heated from 79 to 124° C. over 1.5 hours, no additional distillation is observed.

A higher vacuum (3 to 5 mbar) is applied to the reactor. The tank temperature is gradually raised to 175-180° C. over 5 hours. The content of A13 is 0.12% P via $^{31}P$ NMR analysis. The tank is then heated at 180° C./5 mmHg for 3 hours.

The composition of the final sample is:

A13<0.1% by weight

A13 oxide<0.1% by weight

ABC>99%

The invention claimed is:

1. A flame-retardant mixture of components (A), (B) and optionally (C) having the formula:

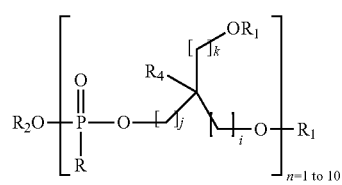

in which:

i, j and k are, independently, equal to 1 to 10,

R is a linear, branched or cyclic alkyl or alkenyl radical, $R_4$ is a proton or a linear, branched or cyclic alkyl or alkenyl radical, $R_2$ is a linear, branched or cyclic alkyl or alkenyl radical or the cyclic phosphonate (I):

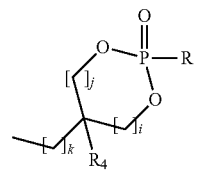

in which i, j, k, R and R4 are as defined above, $R_1$ is:

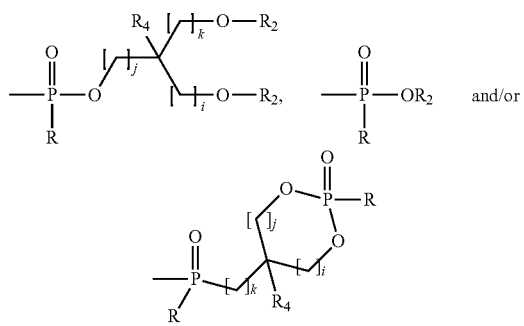

in which $R_2$, $R_4$, R, i, j and k are as defined above;

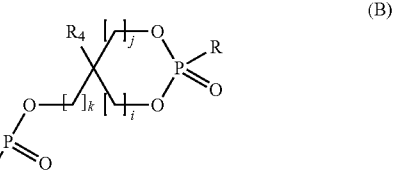

in which $R_2$, $R_4$, R, i, j and k are as defined above; and

in which:

R is a linear, branched or cyclic alkyl or alkenyl radical as defined above, and $R_5$ is a linear, branched or cyclic alkyl or alkenyl radical.

2. The flame-retardant mixture as defined by claim 1, in which R is a proton.

3. The flame-retardant mixture as defined by claim 1, in which components (A), (B) and (C) are present at mole ratios of 1-99%, 1-99% and 0-25%, respectively.

4. The flame-retardant mixture as defined by claim 3, in which components (A), (B) and (C) are present at mole ratios of 30-55%, 30-40% and 5-15%, respectively.

5. The flame-retardant mixture as defined by claim 4, in which:
i, j, k=1,
$R_4$=ethyl,
R=hexyl,
$R_5$=butyl, and
$R_2$=butyl or (I).

6. The flame-retardant mixture as defined by claim 4, in which:
i, j, k=1,
$R_4$=ethyl,
R=butyl,
$R_5$=butyl, and
$R_2$=butyl or (I).

7. The flame-retardant mixture as defined by claim 1, in which:
i, j, k=1,
$R_4$=ethyl,
R=hexyl,
$R_5$=butyl,
$R_2$=butyl or (I).

8. The flame-retardant mixture as defined by claim 1, in which:
i, j, k=1,
$R_4$=ethyl,
R=butyl,
$R_5$=butyl,
$R_2$=butyl or (I).

9. A process for preparing the flame-retardant mixture as defined by claim 1, comprising the following steps:
a) reacting a triol of general formula (IV) with a dialkyl phosphate of general formula (V) to provide an intermediate (VI) comprising a mixture of components (A'), (B') and optionally (C'):

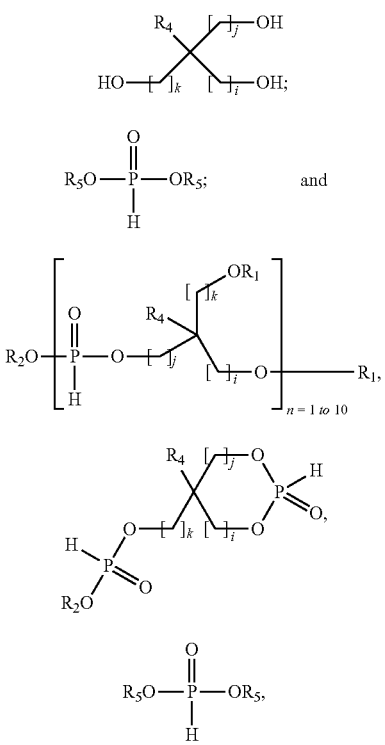

in which:
i, j and k are independently, equal to 1 to 10,
$R_4$ is a proton or a linear, branched or cyclic alkyl or alkenyl radical,
$R_5$ is a linear, branched or cyclic alkyl or alkenyl radical,
$R_2$ is a linear, branched or cyclic alkyl or alkenyl radical or formula (I'):

(I')

and
$R_1$ is:

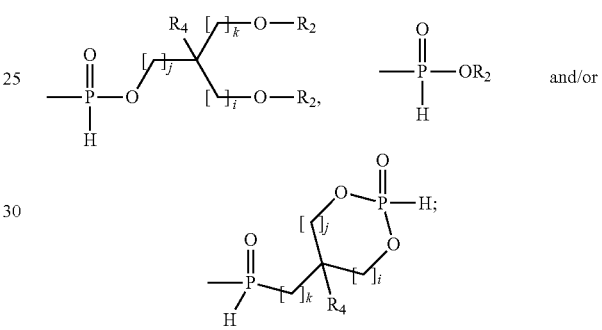

b) reacting the intermediate (VI) with a linear, branched or cyclic alkene or alkyne or a substituted alkene or alkyne containing at least one unsaturated bond, in the presence of a non-oxidizing radical initiator, to partially convert the phosphate into phosphonate, and produce a bicyclic phosphite;
c) removing the bicyclic phosphite produced in the preceding step, via distillation optionally, in the presence of a solvent;
d) reacting the intermediate with a linear, branched or cyclic alkene or alkyne or a substituted alkene or alkyne containing at least one unsaturated bond in the presence of a radical initiator, to provide total conversion of the remaining phosphate of the intermediate; and
e) optionally purifying the product obtained in step d), optionally by distillation.

10. The process as defined by claim 9, in which the non-oxidizing free-radical initiator employed in step b) comprises 2,2'-azobis(2-methyl-butyronitrile).

11. The process as defined by claim 9, in which the initiator employed in step d) comprises di-tert-butyl peroxide.

12. The process as defined by claim 9, in which the triol employed in step a) comprises trimethylolpropane.

13. A porous inorganic compound comprising the flame-retardant mixture as defined by claim 1 absorbed thereon, wherein the porous inorganic compound is selected from the group consisting of an oxide, an inorganic hydroxide and a mineral salt.

14. A thermoplastic composition comprising a thermoplastic material and a flame-retardant mixture as defined by claim 1.

15. A composition comprising a resin and the flame-retardant mixture as defined by claim 1, wherein the resin is selected from the group consisting of an epoxy resin, a polyurethane resin and a phenolic resin.

16. A coating agent for an inorganic material, useful as a functional additive in a polymer matrix, comprising the flame-retardant mixture as defined by claim 1.

17. An inorganic material comprising a treatment of the flame-retardant mixture as defined by claim 1, wherein the inorganic matter is selected from the group consisting of a pigment, a filler and an extender.

18. A composition comprising the flame-retardant mixture as defined by claim 1, wherein the composition is formulated as a paint or varnish.

19. A textile material comprising a treatment of the flame-retardant mixture as defined by claim 1.

* * * * *